United States Patent [19]

McAtee et al.

[11] Patent Number: 5,811,111
[45] Date of Patent: *Sep. 22, 1998

[54] COMPOSITIONS FOR TOPICAL DELIVERY OF ACTIVE INGREDIENTS

[75] Inventors: David Michael McAtee, Fairfield; Lourdes Dessus Albacarys, West Chester; Joseph Anthony Listro, Loveland, all of Ohio

[73] Assignee: The Procter & Gamble Company, Cincinnati, Ohio

[*] Notice: The term of this patent shall not extend beyond the expiration date of Pat. No. 5,665,364.

[21] Appl. No.: 833,016

[22] Filed: Apr. 3, 1997

Related U.S. Application Data

[63] Continuation of Ser. No. 506,149, Jul. 24, 1995, Pat. No. 5,665,364.

[51] Int. Cl.$^6$ .................................................. A61K 7/00
[52] U.S. Cl. ...................... 424/401; 514/844; 514/846
[58] Field of Search ..................... 424/401, 70.19; 510/130, 137, 138, 159; 514/844, 846

[56] References Cited

U.S. PATENT DOCUMENTS

| | | | |
|---|---|---|---|
| 4,166,048 | 8/1979 | Nishimura et al. | 252/546 |
| 4,243,549 | 1/1981 | Messenger et al. | 252/355 |
| 4,246,131 | 1/1981 | Lohr | 252/153 |
| 4,321,256 | 3/1982 | Hasegawa et al. | 424/70 |
| 4,555,360 | 11/1985 | Bissett et al. | 252/541 |
| 4,772,424 | 9/1988 | Greeb | 252/546 |
| 5,246,629 | 9/1993 | Fukumoto et al. | 252/546 |
| 5,387,373 | 2/1995 | Naik | 252/546 |
| 5,607,980 | 3/1997 | McAtee et al. | 514/476 |
| 5,665,364 | 9/1997 | McAtee et al. | 424/401 |

FOREIGN PATENT DOCUMENTS

| | | | |
|---|---|---|---|
| 8703735 | 5/1987 | European Pat. Off. | A61K 7/07 |
| 0 247 832 | 12/1987 | European Pat. Off. | C11D 1/94 |
| 0 373 851 | 6/1990 | European Pat. Off. | C11D 1/94 |
| 681832-A2 | 11/1995 | European Pat. Off. | |
| 3011549 | 10/1981 | Germany | C11D 1/14 |
| 3837985 | 5/1990 | Germany | A61K 7/07 |
| 63-309594 | 12/1988 | Japan | C11D 1/94 |
| 63-313711 | 12/1988 | Japan | A61K 7/06 |
| 01081900 | 3/1989 | Japan | A61K 7/07 |
| 01135898 | 5/1989 | Japan | A61K 7/07 |
| 05017342 | 1/1993 | Japan | A61K 7/50 |
| 05194985 | 8/1993 | Japan | C11D 1/62 |
| 06293620 | 10/1994 | Japan | A61K 7/075 |
| 07025726 | 1/1995 | Japan | A61K 7/02 |
| 1 306 969 | 2/1973 | United Kingdom | C11D 1/12 |
| 91/17237 | 11/1991 | WIPO | C11D 17/00 |
| 95/15150 | 6/1995 | WIPO | A61K 7/50 |
| 95/24179 | 9/1995 | WIPO | A61K 7/00 |
| 96/02225 | 2/1996 | WIPO | A61K 7/00 |
| 96/05798 | 2/1996 | WIPO | A61K 7/00 |
| 96/06595 | 3/1996 | WIPO | A61K 7/48 |

OTHER PUBLICATIONS

J. Garcia Dominguez e tal., International Journal of Cosmetic Science 3, 57–68 (1981) "The inhibitory effect of some amphoteric surfactants on the irritation potential of alkylsulphates".

Chemical Abstracts, vol. 106, No. 106, No. 12, Mar. 23, 1987, Columbus, OH, US; Abstract No. 89959, XP002019636 & JP 61 263 910 A (Shiseido Co. Ltd) Nov. 21, 1986.

*Primary Examiner*—S. Mark Clardy
*Assistant Examiner*—Robert H. Harrison
*Attorney, Agent, or Firm*—Loretta J. Henderson

[57] ABSTRACT

The compositions of the present invention are useful for the topical delivery of a wide variety of active ingredients. These compositions are particularly useful for treating conditions such as acne and its attendant skin lesions, blemishes, and other imperfections. These compositions are nonirritating to the skin and also provide improved skin feel benefits. These compositions can be in the form of leave-on products and products that are rinsed or wiped from the skin after use.

22 Claims, No Drawings

COMPOSITIONS FOR TOPICAL DELIVERY OF ACTIVE INGREDIENTS

This is a continuation of application Ser. No. 08/506,149, filed on Jul. 24, 1995, now U.S. Pat. No. 5,665,376.

TECHNICAL FIELD

The compositions of the present invention are useful for the topical delivery of a wide variety of active ingredients. These compositions are particularly useful for treating conditions such as acne and its attendant skin lesions, blemishes, and other imperfections. These compositions are useful for clarifying the skin and reducing pore size. These compositions are nonirritating to the skin and also provide improved skin feel benefits. These compositions can be in the form of leave-on products and products that are rinsed or wiped from the skin after use.

BACKGROUND OF THE INVENTION

The treatment of human skin with various agents has been undertaken for many year with the goal being to keep the skin in a smooth and supple conditions. Skin has the tendency to dry out when exposed to low humidity or to harsh detergent solutions for extended periods of time. From a physiological standpoint, dryness is a measure of the water content of the skin. Under normal conditions, the water content and vapor pressure of the epidermis are higher than those of the surrounding air, with consequent evaporation of water from the skin surface. Skin becomes dry because of excessive loss of water from its surface which results in loss of water from the stratum corneum. Low humidity speeds up this process, exacerbating the drying of skin.

Continuous and prolonged immersion in soap or detergent solutions can contribute to dryness of the stratum corneum. The reason for this is that the surfactant medium promotes dissolution of the skin surface and horny layer lipids, and the dissolution of the hygroscopic water-soluble components in the skin.

Also, in normal skin, the stratum corneum is shed as individual cells or as small clusters of cells. Skin problems such as dry skin, psoriasis, ichtyosis, dandruff, callus, photodamaged skin, aged skin, and sunburn can be described as disorders of keratinization in which the shedding of stratum corenum cells at the skin surface is altered relative to normal, young, healthy skin. Such alteration results in shedding of large clusters of cells leading to visible scaling of the skin, a build-up of keratinaceous material on the surface or in follicles or ducts, and a rough texture to the skin surface. These conditions can be improved by removal of the outermost keratinaceous material. In other words, by desquamation.

Acne is a condition of the human skin characterized by an excess flow of sebum, or skin oil, from the sebaceous glands located in the pilosebaceous apparatus. Sebum reaches the skin surface through the duct of the hair follicle. The presence of excessive amounts of sebum in the duct and on the skin acts to block or stagnate the continuous flow of sebum from the follicular duct, thus producing a thickening and a solidification of the sebum to form a solid plug known as a comedone. When this process occurs, hyperkeratinization of the follicular opening is stimulated, thus completely closing the duct. The usual results are papules, pustules, or cysts, often contaminated with bacteria which cause secondary infections. Acne is particularly characterized by the presence of comedones, inflammatory papules, pustules, or cysts. The effect of acne ranges from slight skin irritation and pitting to disfiguring scars.

Many topical therapeutic agents are employed in the treatment of acne to prevent the blocking of the folicular duct, to reopen the duct once it has become blocked, to act against the infecting bateria or the thickened sebum, and to provide combinations of each of these actions. The horny outer layer of the skin, which is known as the stratum corneum, is formed of dead cells composed largely of keratin. Therapeutic agents which act to prevent the blocking of the follicular duct by promoting the removal or sloughing off the excess keratin are known as keratolytic agents. However, many anti-acne compositions are harsh and irritating to the skin.

Therefore, there is an ongoing need to effectively deliver a wide variety of active ingredients, particularly anti-acne actives, to the skin, either via direct application of such a composition, or in the case of a cleansing composition, via the cleansing process. There is a need for developing products which are gentle and nonirritating to the skin.

It has been found in the present invention that skin care compositions containing a combination of an amphoteric surfactant and an anionic surfactant, further in combination with an active ingredient, are useful for providing these skin care benefits. When the active ingredient is salicylic acid or benzoyl peroxide, these composition have been found especially useful for treating or cleansing the skin, especially skin that is afflicted with acne. These compositions are found to provide improved anti-acne efficacy. These compositions have been found to be gentle and nonirritating and to leave the skin feeling soft and smooth.

It is therefore an object of the present invention to provide skin care compositions for topical application to the skin.

It is another object of the present invention to provide skin care compositions which are useful for efficiently delivering a wide variety of active ingredients to the skin.

It is another object of the present invention to provide skin care compositions having improved skin conditioning and dryness reducing properties.

It is another object of the present invention to provide compositions which are useful for treating and preventing acne, while being mild and nonirritating to the skin.

It is another object of the present invention to provide skin care compositions which, when in the form of cleansing compositions, are useful for delivering a wide variety of active ingredients to the skin via the cleansing process.

It is another object of the present invention to provide methods for treating the skin.

It is another object of the present invention to provide methods for delivering active ingredients to the skin, to provide methods for treating acne, to provide methods for treating dry skin, to provide methods for cleansing the skin, to provide methods for reducing pore size, to provide methods for clarifying the skin, and to provide methods for desquamating the skin.

These and other objects will become readily apparent from the detailed description which follows.

SUMMARY OF THE INVENTION

The present invention relates to topical personal care compositions comprising:

(a) from about 0.1% to about 20% by weight of an amphoteric surfactant having the following structure

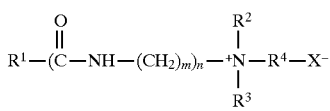

wherein $R^1$ is unsubstituted, saturated or unsaturated, straight or branched chain alkyl having from about 9 to about 22 carbon atoms; m is an integer from 1 to about 3; n is 0 or 1; $R^2$ and $R^3$ are independently selected from alkyl having from 1 to about 3 carbon atoms and monohydroxyalkyl having from 1 to about 3 carbon atoms; $R^4$ is selected from saturated or unsaturated alkyl having from 1 to about 5 carbon atoms and saturated or unsaturated monohydroxyalkyl having from 1 to about 5 carbon atoms; X is selected from the group consisting of $CO_2$, $SO_3$, and $SO_4$; and pharmaceutically acceptable salts of the foregoing compounds;

(b) from about 0.1% to about 20% by weight of an anionic surfactant, (c) from about 0.001% to about 20% of an active ingredient, and (d) from about 40% to about 99.799% by weight water.

The present invention also relates to methods for treating the skin, specifically to methods of treating conditions such as acne, and to methods for conditioning, cleansing, clarifying, reducing pore size, and desquamating the skin, utilizing these foregoing compositions.

The present invention also relates to methods of preparing a composition comprising (a) from about 0.1% to about 20% by weight of an amphoteric surfactant having the following structure

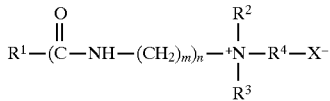

wherein $R^1$ is unsubstituted, saturated or unsaturated, straight or branched chain alkyl having from about 9 to about 22 carbon atoms; m is an integer from 1 to about 3; n is 0 or 1; $R^2$ and $R^3$ are independently selected from alkyl having from 1 to about 3 carbon atoms and monohydroxyalkyl having from 1 to about 3 carbon atoms; $R^4$ is selected from saturated or unsaturated alkyl having from 1 to about 5 carbon atoms and saturated or unsaturated monohydroxyalkyl having from 1 to about 5 carbon atoms; X is selected from the group consisting of $CO_2$, $SO_3$, and $SO_4$; and pharmaceutically acceptable salts of the foregoing compounds;

(b) from about 0.1% to about 20% by weight of an anionic surfactant, (c) from about 0.001% to about 20% of an active ingredient, and (d) from about 40% to about 99.799% by weight water; comprising the steps of:

(i) combining an aqueous solution of said amphoteric surfactant and an aqueous solution of said anionic surfactant to form an aqueous dispersion of a complex of said amphoteric and said anionic surfactant, and (ii) combining said aqueous dispersion of said complex with said active ingredient.

All percentages and ratios used herein are by weight of the total composition and all measurements made are at 25° C. or room temperature, unless otherwise designated. All weight percentages, unless otherwise indicated, are on an actives weight basis. The invention hereof can comprise, consist of, or consist essentially of, the essential as well as the optional ingredients and additional components described herein.

DETAILED DESCRIPTION OF THE INVENTION

The compositions of the present invention are useful for delivering a wide variety of active ingredients to the surface of the skin. These compositions, when they contain anti-acne actives provide improved anti-acne efficacy versus conventional formulas.

Without being limited by theory it is believed that the amphoteric surfactant of these compositions complexes with the anionic surfactant. This postulated complex is believed to be highly stable relative to the individual surfactant components. This complex is useful for aiding in the delivery of the active ingredients to the skin, thereby aiding their efficacy. In the case of a cleansing composition, this complex tends to deposit out from the composition thereby helping to carry the active ingredients to the skin's surface during the cleansing process. Because the postulated complex contains an amphoteric and an anionic surfactant, this complex is also effective for cleansing the skin and for promoting the desquamation process. Because the charges on the individual surfactants are complexed, the surfactants are rendered less harsh and irritating to the skin versus the free surfactants.

The compositions of the present invention can be formulated into a wide variety of product types including, but not limited to creams, lotions, mousses, sprays, "rinse-off" cleansers, "water-less" cleansers, bars, gels, and the like. The term "rinse-off," as used herein, means that the composition is in the form that can be used in a cleansing process whereby the composition is ultimately rinsed or washed from the skin with water to complete the cleansing process. The term "water-less," as used herein, means that the composition is in a form that can be used in a cleansing process without water whereby the composition is typically removed by wiping with a device such as a cotton ball, a cotton pad, a tissue, a towel, and the like.

The term "pharmaceutically-acceptable," as used herein, means that the compositions and components thereof so described are of sufficiently high purity and are suitable for use in contact with human skin and tissues without undue toxicity, irritation, incompatibility, instability, allergic response, and the like.

The term "pharmaceutically-acceptable salts," as used herein means any of the commonly-used salts that are suitable for use in contact with human skin and tissues without undue toxicity, irritation, incompatibility, instability, allergic response, and the like.

Amphoteric Surfactant

The compositions of the present invention comprise from about 0.1% to about 20%, more preferably from about 0.2% to about 10%, and most preferably from about 0.5% to about 5% of an amphoteric surfactant.

The term "amphoteric surfactant," as used herein, is also intended to encompass zwitterionic surfactants, which are well known to formulators skilled in the art as a subset of amphoteric surfactants.

A wide variety of amphoteric surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Nonlimiting examples of amphoteric surfactants useful in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety.

Preferred amphoteric or zwitterionic surfactants are the betaines, sultaines, and hydroxysultaines. Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonzaine 16SP from Lonza Corp.), lauryl bis-(2-hydroxyethyl) carboxymethyl betaine, steryl bis-(2-hydroxypropyl) carboxymethyl betaine, oleyl dimethyl gamma-carboxypropyl betaine, lauryl bis-(2-hydroxypropyl)alpha-carboxyethyl betaine, coco dimethyl sulfopropyl betaine, stearyl dimethyl sulfopropyl betaine, stearyl betaine, lauryl dimethyl sulfoethyl betaine, lauryl bis-(2_hydroxyethyl) sulfopropyl betaine, and amidobetaines and amidosulfobetaines (wherein the RCONH(CH$_2$)$_3$ radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Examples of sultaines and hydroxysultaines include materials such as cocamidopropyl hydroxysultaine (available as Miratain CBS from Rhone-Poulenc).

Preferred for use herein are amphoteric surfactants having the following structure:

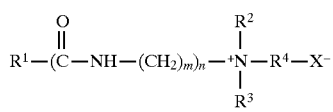

wherein R$^1$ is unsubstituted, saturated or unsaturated, straight or branched chain alkyl having from about 9 to about 22 carbon atoms. Preferred R$^2$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably about 3; n is either 0 or 1, preferably 1; R$^2$ and R$^3$ are independently selected from the group consisting of alkyl having from 1 to about 3 carbon atoms, unsubstituted or mono-substituted with hydroxy, preferred R$^2$ and R$^3$ are CH$_3$; X is selected from the group consisting of CO$_2$, SO$_3$ and SO$_4$; R$^4$ is selected from the group consisting of saturated or unsaturated, straight or branched chain alkyl, unsubstituted or monosubstituted with hydroxy, having from 1 to about 5 carbon atoms. When X is CO$_2$, R$^4$ preferably has 1 or 3 carbons atoms, more preferably 1 carbons atom. When X is SO$_3$ or SO$_4$, R$^4$ preferably has from about 2 to about 4 carbon atoms, more preferably 3 carbon atoms.

Examples of amphoteric surfactants of the present invention include the following compounds:
Cetyl dimethyl betaine (this material also has the CTFA designation cetyl betaine)

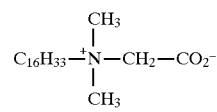

Cocamidopropylbetaine

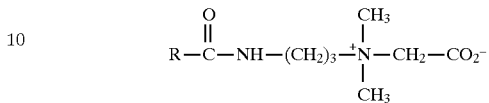

wherein R has from about 9 to about 13 carbon atoms
Cocamidopropyl hydroxy sultaine

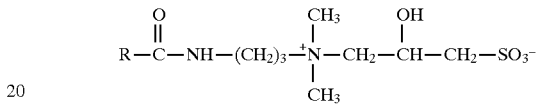

wherein R has from about 9 to about 13 carbons atoms,
Stearyl dimethyl betaine

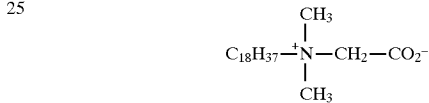

and
Behenyl Betaine

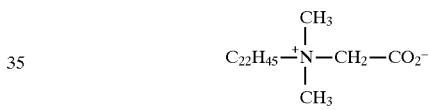

Preferred amphoteric surfactants of the present invention include cetyl dimethyl betaine, cocoamidopropyl betaine, stearyl dimethyl betaines, and cocoamidopropyl hydroxy sultaine. Still more preferred are cetyl dimethyl betaine, stearyl dimethyl betaine, and cocamidopropyl betaine. Most preferred is cetyl dimethyl betaine.

Examples of other useful amphoteric surfactants are alkyliminoacetates, and iminodialkanoates and aminoalkanoates of the formulas RN[CH$_2$)$_m$CO$_2$M]$_2$ and RNH(CH$_2$)$_m$CO$_2$M wherein m is from 1 to 4, R is a C$_8$–C$_{22}$ alkyl or alkenyl, and M is H, alkali metal, alkaline earth metal ammonium, or alkanolammonium. Also included are imidazolinium and ammonium derivatives. Specific examples of suitable amphoteric surfactants include sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072 which is incorporated herein by reference in its entirety; N-higher alkyl aspartic acids such as those produced according to the teaching of U.S. Pat. No. 2,438,091 which is incorporated herein by reference in its entirety; and the products sold under the trade name "Miranol" and described in U.S. Pat. No. 2,528,378, which is incorporated herein by reference in its entirety. Other examples of useful amphoterics include phosphates, such as coamidopropyl PG-dimonium chloride phosphate (commercially available as Monaquat PTC, from Mona Corp.).

Anionic Surfactant

The compositions of the present invention comprise from about 0.1% to about 20%, more preferably from about 0.2% to about 10%, and most preferably from about 0.5% to about 5% of an anionic surfactant.

Nonlimiting examples of anionic surfactants useful in the compositions of the present invention are disclosed in McCutcheon's, *Detergents and Emulsifiers*, North American edition (1986), published by allured Publishing Corporation; McCutcheon's, *Functional Materials*, North American Edition (1992); and U.S. Pat. No. 3,929,678, to Laughlin et al., issued Dec. 30, 1975 all of which are incorporated by reference herein in their entirety.

A wide variety of anionic surfactants are useful herein. Nonlimiting examples of anionic surfactants include the alkoyl isethionates, and the alkyl and alkyl ether sulfates. The alkoyl isethionates typically have the formula RCO—OCH$_2$CH$_2$SO$_3$M wherein R is alkyl or alkenyl of from about 10 to about 30 carbon atoms, and M is a water-soluble cation such as ammonium, sodium, potassium and triethanolamine. Nonlimiting examples of these isethionates include those alkoyl isethionates selected from the group consisting of ammonium cocoyl isethionate, sodium cocoyl isethionate, sodium lauroyl isethionate, sodium stearoyl isethionate, and mixtures thereof.

The alkyl and alkyl ether sulfates typically have the respective formulae ROSO$_3$M and RO(C$_2$H$_4$O)$_x$SO$_3$M, wherein R is alkyl or alkenyl of from about 10 to about 30 carbon atoms, x is from about 1 to about 10, and M is a water-soluble cation such as ammonium, sodium, potassium and triethanoloamine. Another suitable class of anionic surfactants are the water-soluble salts of the organic, sulfuric acid reaction products of the general formula:

$$R_1-SO_3-M$$

wherein R$_1$ is chosen from the group consisting of a straight or branched chain, saturated aliphatic hydrocarbon radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and b-alkyloxy alkane sulfonates. Examples of these materials are sodium lauryl sulfate and ammonium lauryl sulfate.

Other anionic materials include the sarcosinates nonlimiting examples of which include sodium lauroyl sarcosinate, sodium cocoyl sarcosinate, and ammonium lauroyl sarcosinate.

Other anionic materials useful herein are soaps (i.e. alkali metal salts, e.g., sodium or potassium salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil coconut oil, soybean oil, castor oil, tallow, lard, etc.) The fatty acids can also be synthetically prepared. Soaps are described in more detail in U.S. Pat. No. 4,557,853, cited above.

Other anionic materials include phosphates such as monoalkyl, dialkyl, and trialkylphosphate salts.

Other anionic materials include alkanoyl sarcosinates corresponding to the formula RCON(CH$_3$)CH$_2$CH$_2$CO$_2$M wherein R is alkyl or alkenyl of about 10 to about 20 carbon atoms, and M is a water-soluble cation such as ammonium, sodium, potassium and trialkanolamine (e.g., triethanolamine), a preferred example of which is sodium lauroyl sarcosinate.

Nonlimiting examples of preferred anionic surfactants useful herein include those selected from the group consisting of sodium lauryl sulfate, ammonium lauryl sulfate, ammonium cetyl sulfate, sodium cetyl sulfate, sodium stearyl sulfate, ammonium cocoyl isethionate, sodium lauroyl isethionate, sodium lauroyl sarcosinate, and mixtures thereof.

Especially preferred for use herein is sodium lauryl sulfate.

Active Ingredients

The compositions of the present invention comprise a safe and effective amount of one or more active ingredients or pharmaceutically-acceptable salts thereof.

The term "safe and effective amount" as used herein, means an amount of an active ingredient high enough to modify the condition to be treated or to deliver the desired skin benefit, but low enough to avoid serious side effects, at a reasonable benefit to risk ratio within the scope of sound medial judgment. What is a safe and effective amount of active ingredient will vary with the specific active, the ability of the active to penetrate through the skin, the age, health condition, and skin condition of the user, and other like factors.

Typically, the active ingredients of the present invention comprise from about 0.001% to about 20%, preferably from about 0.01% to about 15%, and more preferably from about 0.025% to about 10% by weight of the composition.

The active ingredients useful herein can be categorized by their therapeutic benefit or their postulated mode of action. However, it is to be understood that the active ingredients useful herein can in some instances, provide more than one therapeutic benefit or operate via more than one mode of action. Therefore, classifications herein are made for the sake of convenience and are not intended to limit the active ingredient to that particular application or applications listed. Also, pharmaceutically-acceptable salts of these active ingredients are useful herein. The following active ingredients are useful in the compositions of the present invention.

Anti-acne Actives:

Examples of useful anti-acne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, actopirox, tetracycline, 2,4, 4'-trichloro-2°-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives:

Examples of antiwrinkle and anti-skin atrophy actives include retinoic acid and its derivatives (e.g., cis and trans); retinol; retinyl esters; salicylic acid and derivatives thereof; sulfur-containing D and L amino acids and their derivatives and salts, particularly the N-acetyl derivatives, a preferred example of which is N-acetyl-L-cysteine; thiols, eg. ethane thiol; alpha-hydroxy acids, e.g. glycolic acid, and lactic acid;

phytic acid, lipoic acid; lysophosphatidic acid, and skin peel agents (e.g., phenol and the like).

Non-Steroidal Anti-Inflammatory Actives (NSAIDS):

Examples of NSAIDS include the following categories: propionic acid derivatives; acetic acid derivatives; fenamic acid derivatives; biphenylcarboxylic acid derivatives; and oxicams. All of these NSAIDS are fully described in U.S. Pat. No. 4,985,459 to Sunshine et al., issued Jan. 15, 1991, incorporated by reference herein in its entirety. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen and bucloxis acid. Also useful are the steroidal anti-inflammatory drugs including hydrocortisone and the like.

Topical Anesthetics:

Examples of topical anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof.

Antimicrobial and Antifungal Actives:

Examples of antimicrobial and antifungal actives include $\beta$-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chorhexidine, chlortetracycline, oxytetracycline, clindamycin, ethambutol, hexamidine isethionate, metronidazole, pentamidine, gentamicin, kanamycin, lineomycin, methacycline, methanamine, minocycline, neomycin, netilmicin, paromomycin, streptomycin, tobramycin, miconazole, tetracycline hydrochoride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate and clotrimazole.

Preferred examples of actives useful herein include those selected from the group consisting of salicylic acid, benzoyl peroxide, 3-hydroxy benzoic acid, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, phytic acid, N-acetyl-L-cysteine, lipoic acid, azelaic acid, arachidonic acid, benzoylperoxide, tetracycline, ibuprofen, naproxen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, neocycin sulfate, and mixtures thereof.

More preferred examples of actives useful herein include those selected from the group consisting of salicylic acid, acetyl salicylic acid, cis-retinoic acid, trans-retinoic acid, retinol, phytic acid, N-acetyl-L-cystein, lipoic acid, azelaic acid, tetracycline, ibuprofen, naproxen, acetominophen, hydrocortisone, resorcinol, phenoxyethanol, phenoxypropanol, phenoxyisopropanol, 2,4,4'-trichloro-2'-hydroxy diphenyl ether, 3,4,4'-trichlorocarbanilide, octopirox, and mixtures thereof.

More preferred examples of actives useful herein include those selected from the group consisting of salicylic acid, benzoyl peroxide, cis-retinoic acid, trans-retinoic acid, retinol, phytic acid, N-acetyl L-cysteine, azelaic acid, lipoic acid, resorcinol, lactic acid, glycolic acid, ibuprofen, naproxen, hydrocortisone, phenoxyethanol, phenoxypropanol, phenoxyisopropanol, 2,4,4,'-trichloro-2'-hydroxy diphenyl ether, 3,4,4,'-trichlorocarbanilide, and mixtures thereof.

Most preferred are salicylic acid and benozyl peroxide.

Water

The composition of the present invention comprise from about 40% to about 99.799%, more preferably from about 60% to about 95%, and most preferably from about 70% to about 90% of water. The exact level of water will depend upon the form of the product and the desired moisture content.

Additional Components

The compositions of the present invention can comprise a wide range of additional components. The *CTFA Cosmetic Ingredient Handbook*, Second Edition, 1992, which is incorporated by reference herein in its entirety, describes a wide variety of cosmetic and pharmaceutical ingredients commonly used in the skin care industry, which are suitable for use in the compositions of the present invention. Nonlimiting examples of functional classes of ingredients are described at page 537 of this reference. Examples of these functional classes include: absorbents, abrasives, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, platicizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include emulsifiers, sequestrants, skin sensates, and the like.

Nonlimiting examples of these additional components cited in the *CTFA Cosmetic Ingredient Handbook*, as well as other materials useful herein, include the following: vitamins and derivatives thereof [e.g., vitamin C, Vitamin A (i.e. retinoic acid), retinol, retinoids, panthenol, panthenol esters, tocopherol, tocopherol esters, and the like]; oil or sebum control agents such as clays silicones and drug actives; sunscreening agents; other silicone materials such as dimethiconol, dimethocone copolyol, and amodimethicone, and the like); anti-oxidants; anti-microbial agents; preservatives; emulsifiers; polyethyleneglycols and polypropyleneglycols; polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; anti-acne medicaments (e.g., resorcinol, sulfur, salicylic acid, erythromycin, zinc, and the like); skin bleaching (or lightening) agents including but not limited to hydroquinone, kojic acid; antioxidants; chelators and sequestrants; thickening agents such as carbomers (homopolymers of acrylic acid crosslinked with an allyl ether of pantaerythritol or an allyl ether of sucrose), crosslinked and noncrosslinked nonionic and cationic polyacrylamides [e.g., Salcare® SC92 which has the CTGA designation polyquaternium 32 (and) mineral oil, and Salcare® SC95 which has the CTFA designation polyquaternium 37 (and) mineral oil (and) PPG-1 trideceth-6, and the nonionic Seppi-Gel polyacrylamides available from Seppic Corp.]; proteins and peptides; enzymes; ceramides; aesthetic components such as fragrances, pigments, coloring, essential oils, skin senates, astringents, skin soothing agents, skin healing agents and the like, [nonlimiting examples of these aesthetic components include clove oil, menthol, camphor, eucalyptus oil, eugenol, menthyl lactate, witch hazel distillate, bisabolol, dipotassium glycyrrhizinate and the like]; and skin conditioning agents such as urea and glycerol, and also the propoxylated glycerols described in U.S. Pat. No. 4,976,953, to Orr et al., issued Dec. 11, 1990, which is incorporated by reference herein in its entirety.

Some of these additional ingredients are described in more detail below.

Additional Surfactants

The compositions of the present invention, in addition to the required surfactant materials, can comprise additional surfactant materials. Especially useful are cationic and nonionic surfactants.

The compositions of the present invention can comprise from about 0.1% to about 15%, more preferably from about 0.2% to about 10%, and more preferably from about 0.5% to about 5% of a cationic surfactant.

Nonlimiting examples of cationic surfactants useful in the compositions of the present invention are disclosed in McCutcheon's, *Detergents and Emulsifiers*, North American edition (1986), published by allured Publishing Corporation; and McCutcheon's, *Functional Materials*, North American Edition (1992); both of which are incorporated by reference herein in their entirety. Without being limited by theory, it is believed that such cationic materials can also provide an antimicrobial effect to the compositions herein. Therefore, cationic materials having antimicrobial properties are highly useful herein.

Nonlimiting examples of cationic surfactants useful herein include cationic ammonium salts such as those having the formula:

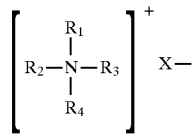

wherein $R_1$, is selected from an alkyl group having from about 12 to about 22 carbon atoms, or aromatic, aryl or alkaryl groups having from about 12 to about 22 carbon atoms; $R_2$, $R_3$, and $R_4$ are independently selected from hydrogen, an alkyl group having from about 1 to about 22 carbon atoms, or aromatic, aryl or alkaryl groups having from about 12 to about 22 carbon atoms; and X is an anion selected from chloride, bromide, iodide, acetate, phosphate, nitrate, sulfate, methyl sulfate, ethyl sulfate, tosylate, lactate, citrate, glycolate, and mixtures thereof. Additionally, the alkyl groups can also contain either linkages, or hydroxy or amino group substituents (e.g., the alkyl groups can contain polyethylene glycol and polyproylene glycol moieties).

More preferably, $R_2$ is an alkyl group having from about 12 to about 22 carbon atoms; $R_2$ is selected from H or an alkyl group having from about 1 to about 22 carbons atoms; $R_3$ and $R_4$ are independently selected from H or an alkyl group having from about 1 to about 3 carbon atoms; and X is as described in the previous paragraph.

Most preferably, $R_2$ is an alkyl group having from about 12 to about 22 carbon atoms; $R_2$, $R_3$, and $R_4$ are selected from H or an alkyl group having from about 1 to about 3 carbon atoms; and X is a described previously.

Alternatively, other useful cationic surfactants include amino-amides, wherein in the above structure $R_2$ is alternatively $R_5CO-(CH_2)_n-$, wherein $R_5$ is an alkyl group having from about 12 to about 22 carbon atoms, and n is an integer from about 2 to about 6, more preferably from about 2 to about 4, and most preferably from about 2 to about 3. Nonlimiting examples of these cationic emulsifiers include stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Nonlimiting examples of quaternary ammonium salt cationic surfactants include those selected from the group consisting of cetyl ammonium chloride, cetyl ammonium bromide, lauryl ammonium chloride, lauryl ammonium bromide, stearyl ammonium chloride, stearyl ammonium bromide, cetyl dimethyl ammonium chloride, cetyl dimethyl ammonium bromide, lauryl dimethyl ammonium chloride, lauryl dimethyl ammonium bromide, stearyl dimethyl ammonium chloride, stearyl dimethyl ammonium bromide, cetyl trimethyl ammonium chloride, cetyl trimethyl ammonium bromide, lauryl trimethyl ammonium chloride, lauryl trimethyl ammonium bromide, stearyl trimethyl ammonium chloride, stearyl trimethyl ammonium bromide, lauryl dimethyl ammonium chloride, stearyl dimethyl cetyl ditallow dimethyl ammonium chloride, diectyl ammonium chloride, decetyl ammonium bromide, dilauryl ammonium chloride, dilauryl ammonium bromide, distearyl ammonium chloride, distearyl ammonium bromide, dicetyl methyl ammonium chloride, dicetyl methyl ammonium bromide, dilauryl methyl ammonium chloride, dilauryl methyl ammonium bromide, distearyl methyl ammonium chloride, distearyl dimethyl ammonium chloride, distearyl methyl ammonium bromide, and mixtures thereof. Additional quaternary ammonium salts include those wherein C12 to C22 alkyl carbon chain is derived from a tallow fatty acid or from a coconut fatty acid. The term "tallow" refers to an alkyl group derived from tallow fatty acids (usually hydrogenated tallow fatty acids), which generally have mixtures of alkyl chains in the C16 to C18 range. The term "coconut" refers to an alkyl group derived from a coconut fatty acid, which generally have mixtures of alkyl chains in the C12 to C14 range. Examples of quaternary ammonium slats derived from these tallow and coconut sources include ditallow dimethyl ammonium chloride, ditallow dimethyl ammonium methyl sulfate, di(hydrogenated tallow) dimethyl ammonium chloride, di(hydrogenated tallow) dimethyl ammonium acetate, ditallow dipropyl ammonium phosphate, ditallow dimethyl ammonium nitrate, di(coconutalkyl)dimethyl ammonium chloride, di(coconutalkyl)dimethyl ammonium bromide, tallow ammonium chloride, coconut ammonium chloride, stearamidopropyl PG-dimonium chloride phosphate, stearamidopropyl ethyldimonium ethosulfate, stearamidopropyl dimethyl (myristyl acetate) ammonium chloride, stearamidopropyl dimethyl cetearyl ammonium tosylate, stearamidopropyl dimethyl ammonium chloride, stearamidopropyl dimethyl ammonium lactate, and mixtures thereof.

Preferred cationic surfactants useful herein include those selected from the group consisting of dilauryl dimethyl ammonium chloride, distearyl dimethyl ammonium chloride, dimyristyl dimethyl ammonium chloride, dipalmityl dimethyl ammonium chloride, distearyl dimethyl ammonium chloride, and mixtures thereof.

The compositions of the present invention can comprise from about 0.1% to about 15%, more preferably from about 0.2% to about 10%, and more preferably from about 0.5% to about 5% of a nonionic surfactant.

Nonlimiting examples of nonionic surfactants for use in the compositions of the present invention are disclosed in McCutcheon's, *Detergents and Emulsifiers*, North American edition (1986), published by allured Publishing Corporation; and McCutcheon's, *Functional Materials,* North American Edition (1992); both of which are incorporated by reference herein in their entirety.

Among the nonionic surfactants what are useful herein are those than can be broadly defined as condensation products of long chain alcohols, e.g. C8–30 alcohols, with sugar or starch polymers, i.e., glycosides. These compounds can be represented by the formula $(S)_n$—O—R wherein S is a sugar moiety such as glucose, fructose, mannose, and galactose; n is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol, and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600CS and 625 CS from Henkel).

Other useful nonionic surfactants include the condensation products of alkylene oxides with fatty acids (i.e. alkylene oxide esters of fatty acids). These materials have the general formula $RCO(X)_nOH$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 1 to about 100. Other nonionic surfactants are the condensation products of alkylene oxides with 2 moles of fatty acids (i.e. alkylene oxide diesters of fatty acids). These materials have the general formula $RCO(X)_nOOCR$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 1 to about 100. Other nonionic surfactants are the condensation products of alkylene oxides with fatty alcohols (i.e. alkylene oxide ethers of fatty alcohols). These materials have the general formula $R(X)_nOR'$ wherein R is a C10–30 alkyl group, X is —OCH$_2$CH$_2$— (i.e. derived from ethylene glycol or oxide) or —OCH$_2$CHCH$_3$— (i.e. derived from propylene glycol or oxide), and n is an integer from about 1 to about 100 and R' is H or a C10–30 alkyl group. Still other nonionic surfactants are the condensation products of alkylene oxides with both fatty acids and fatty alcohols [i.e. wherein the polyalkylene oxide portion is esterified on one end with a fatty acid and esterified (i.e. connected via an ether linkage) on the other end with a fatty alcohol]. These materials have the general formula $RCO(X)_nOR'$ wherein R and R' are C10–30 alkyl groups, X is —OCH$_2$CH$_2$(i.e. derived from ethylene glycol or oxide) or —OCH$_2$CHCH$_3$— (derived from propylene glycol or oxide),and n is an integer from about 1 to about 100. Nonlimiting examples of these alkylene oxide derived nonionic surfactants include ceteth-1, ceteth-2, ceteth-6, ceteth-10, ceteth-12, ceteareth-2, ceteareth-6, ceteareth-10, ceteareth-12, steareth-1, steareth-2, steareth-6, steareth-10, steareth-12, PEG-2 stearate, PEG-4 stearate, PEG-6 stearate, PEG-10 stearate, PEG-12 stearate, steareth-21, PEG-20 glyceryl stearate, PEG-80 glyceryl tallowate, PPG-10 glyceryl stearate, PEG-30 glyceryl cocoate, PEG-80 glyceryl cocoate, PEG-200 glyceryl tallowate, PEG-8 dilaurate, PEG-10 distearate, and mixtures thereof.

Still other useful nonionic surfactants include polyhydroxy fatty acid amide surfactants corresponding to the structural formula:

wherein: $R^1$ is H, $C_1$–$C_4$ alkyl, 2-hydroxyethyl, 2-hydroxypropyl, preferably $C_1$–$C_4$ alkyl, more preferably methyl or ethyl, most preferably methyl; $R^2$ is $C_5$–$C_{31}$ alkyl or alkenyl, preferably $C_7$–$C_{19}$ alkyl or alkenyl, more preferably $C_9$–$C_{17}$ alkyl or alkenyl, most preferably $C_{11}$–$C_{15}$ alkyl or alkenyl; and Z is a polhydroxyhydrocarbyl moiety having a linear hydrocarbyl chain with a least 3 hydroxyls directly connected to the chain, or an alkoxylated derivative (preferably ethoxylated or propoxylated) thereof. Z preferably is a sugar moiety selected from the group consisting of glucose, fructose, maltose, lactose, galactose, mannose, xylose, and mixtures thereof. An especially preferred surfactant corresponding to the above structure is coconut alkyl N-methyl glucoside amide (i.e., wherein the $R^2CO$— moiety is derived from coconut oil fatty acids). Processes for making compositions containing polyhydroxy fatty acid amides are disclosed, for example, in G.B. Patent Specification 809, 060, published Feb. 18, 1959, by Thomas Hedley & Co., Ltd.; U.S. Pat. No. 2,965,576, to E. R. Wilson, issued Dec. 20, 1960; U.S. Pat. No. 2,703,798, to A. M. Schwartz, issued Mar. 8, 1955; and U.S. Pat. No. 1,985,424, to Piggott, issued Dec. 25, 1934; which are incorporated herein by reference in their entirety.

Humectants and Moisturizers

The compositions of the present invention can also comprise one or more humectants or moisturizers. A variety of these materials can be employed and each can be present at a level of from about 0.1% to about 20%, more preferably from about 0.5% to about 10%, and most preferably from about 1% to about 5%. Nonlimiting examples of humectants include materials selected from the group consisting of guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycols; sugars and starches; sugar and starch derivatives (e.g., alkoxylated glucose); hyaluronic acid; lactamide monoethanolamine; acetamide monoethanolamine; and mixtures thereof.

Also, useful are propoxylated glycerols as described in U.S. Pat. No. 4,976,953, or Orr et al., issued Dec. 11, 1990, which is incorporated by reference herein in its entirety.

An especially preferred humectant for use herein is glycerol.

Insoluble Particles

The compositions of the present invention can comprise from about 0.1% to about 20%, more preferably from about 0.25% to about 15%, and most preferably from about 0.5% to about 10%, based on the weight of the total composition, of insoluble particles which are useful for enhancing the cleansing effect, when the compositions of the present invention are in the form of a cleansing composition.

The term "insoluble", as used herein, means that the particles are essentially insoluble in the compositions of the present invention. In particular, the insoluble particles should have a solubility less than about 1 gram per 100 grams of composition at 25° C., preferably less than about 0.5 grams per 100 grams of composition at 25° C., and more preferably less than about 0.1 grams per 100 grams of composition at 25° C.

Useful herein are both micronized and conventional size insoluble particles. The micronized particles, for the most part, are of a size that is below the tactile threshold and are essentially nonabrasive to the skin. The conventional size particles are tactilely perceptible and are added for the scrubbing and abrasive effect which they provide.

The micronized particles have a mean particle size diameter and particle size distribution such that they are below the tactile perception threshold of most users, and yet are not so small as to be ineffective for aiding in oil, dirt, and debris (e.g., make-up) removal. It is found herein that particles having a means particle size diameter greater than about 75 microns are tactilely perceived during the cleansing process and it is important to minimize the amount of these larger particles if it is desired that the particles not be felt by the user. Conversely, it is found that particles having a mean particle size diameter of less than about 1 to about 5 microns are generally less effective for providing a cleansing benefit. Without being limited by theory, it is believed that the micronized cleansing particles should be of a size that is on the order of the thickness of the dirt, oil, or debris layer to be cleaned away. This layer is believed to be on the order of a few microns in thickness in most instances. It is therefore found in the present invention that the micronized particles should have a means particle size diameter from about 1 to about 75 microns, more preferably from about 15 to about 60 microns, and most preferably from about 20 to about 50 microns, so as to provide effective cleansing without being tactilely perceptible. Particles having a wide range of shapes, surface characteristics, and hardness characteristics can be utilized herein provided the particle size requirements are met. Micronized particles of the present invention can be derived from a wide variety of materials including those derived from inorganic, organic, natural, and synthetic sources. Nonlimiting examples of these materials include those selected from the group consisting of almond meal, alumina, aluminum oxide, aluminum silicate, apricot seed powder, attapulgite, barley flour, bismuth oxychloride, boron nitride, calcium carbonate, calcium phosphate, calcium pyrophosphate, calcium sulfate, cellulose, chalk, chitin, clay, corn cob meal, corn cob powder, corn flour, corn meal, corn starch, diatomaceous earth, dicalcium phosphate, dicalcium phosphate dihydrate, fullers earth, hydrated silica, hydroxyapatite, iron oxide, jojoba seed powder, kaolin, loofah, magnesium trisilicate, mica, microcrystalline cellulose, montmorillonite, oat bran, oat flour, oatmeal, peach pit powder, pecan shell powder, polybutylene, polyethylene, polyisobutylene, polymethylstyrene, polypropylene, polystyrene, polyurethane, nylon, teflon (i.e., polytetrafluoroethylene), polyhalogenated olefins, pumice rice bran, rye flour, sericite, silica, silk, sodium bicarbonate, sodium silicoaluminate, soy four synthetic hectorite, talc, tin oxide, titanium dioxide, tricalcium phosphate, walnut shell powder, wheat bran, wheat flour, wheat starch, zirconium silicate, and mixtures thereof. Also useful are micronized particles made from mixed polymers (e.g., copolymers, terpolymers, etc.), such as polyethylene/polypropylene copolymer, polyethylene/propylene/isobutylene copolymer, polyethylene/styrene copolymer, and the like. Typically, the polymeric and mixed polymeric particles are treated via an oxidation process to destroy impurities and the like. The polymeric and mixed polymeric particles can also optionally be crosslinked with a variety of common crosslinking agents, nonlimiting examples of which include butadiene, divinyl benzene, methylebisacrylamide, allyl ethers of suscrose, allyl ethers of pentaerythritol, and mixtures thereof. Other examples of useful micronized particles include waxes and resins such as paraffins, carnuba wax, ozekerite wax, candellila wax, urea-formaldehyde resins, and the like. When such waxes and resins are used herein it is important that these materials are solids at ambient and skin temperatures.

Among the preferred water-insoluble, micronized particulate materials useful herein are the synthetic polymeric particles selected from the group consisting of polybutylene, polyethylene, polyisobutylene, polymethylstyrene, polypropylene, polystyrene, polyurethane, nylon, teflon, and mixtures thereof. Most preferred are polyethylene and polypropylene micronized particles, with the oxidized versions of these materials being especially preferred. Examples of commercially available particles useful herein include the ACumist™ micronized polyethylene waxes available from Allied Signal (Morristown, N.J.) available as the A, B, C, and D series in a variety of average particle sizes ranging from 5 microns to 60 microns. Preferred are the ACumist™ A-25, A-30, and A-45 oxidized polyethylene particles having a mean particle size of 25, 30, and 45 microns, respectively. Examples of commercially available polypropylene particles include Propyltex series available from Micro Powders (Dartek).

The conventional size insoluble particles are well-known to formulation chemists in the art. These particles typically have larger particle sizes than the micronized particles described herein. These particles generally have an average particle size diameter that is about 75 microns or greater, which is about the tactile threshold described above. These conventional size particles typically have average particle sizes ranging up to about 400 microns and larger. These particles can be made from the same materials as for the micronized particles just described. Among the preferred conventional size particulate materials useful herein are the synthetic polymeric particles selected from the group consisting of polybutylene, polyethylene, polyisobutylene, polymethylstyrene, polypropylene, polystyrene, polyurethane, nylon, teflon, and mixtures thereof. Most preferred are polyethylene and polypropylene micronized particles, with the oxidized versions of these materials being especially preferred. An example of a commercially available conventional size particle useful herein is ACuscrub™ 51, available from Allied Signal (Morristown, N.J.) having a mean particle size of about 125 microns.

Emulsifiers

The compositions herein can comprise various emulsifiers. These emulsifiers are useful for emulsifying the various carrier components of the compositions herein. Suitable emulsifiers can include any of a wide variety of nonionic, cationic, anionic, and zwitterionic emulsifiers disclosed in the prior patents and other references. See McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; there four references are incorporated herein by reference in their entirety.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

The emulsifiers can be used individually or as a mixture of two or more and can comprise from about 0.1% to about 10% more preferably from about 1% to about 7%, and most preferably from about 1% to about 5% of the compositions of the present invention.

Oils

The compositions of the present invention can comprise from about 0.25% to about 40%, preferably from about 0.5% to about 25%, and more preferably from about 0.75% to about 15% of an oil selected from the group consisting of mineral oil, petrolatum, C7–C40 branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, polydialkylsiloxanes, polydiarylsiloxanes, polyalkarylsiloxanes, cyclomethicones having 3 to 9 silicon atoms, vegetable oils, hydrogenated vegetable oils, polypropylene glycols, polypropylene glycol C4–C20 alkyl ethers, di C8–C30 alkyl ethers, and mixtures thereof.

The oil materials generally having low solubility in water, generally less than about 1% by weight at 25° C. Nonlimiting examples of suitable oil components include, but are not limited to, the following materials. Some of these materials are further described in U.S. Pat. No. 4,919,934, to Deckner et al., issued Apr. 24, 1990, which is incorporated herein by reference in its entirety.

Mineral oil, which is also known as petrolatum liquid, is a mixture of liquid hydrocarbons obtained from petroleum. See The Merck Index, Tenth Edition, Entry 7048, p. 1033 (1983) and International Cosmetic Ingredient Dictionary, Fifth Edition, vol. 1, p. 415–417 (1993), which are incorporated by reference herein in their entirety.

Petrolatum, which is also known as petroleum jelly, is a colloidal system of nonstraight-chain solid hydrocarbons and high-boiling liquid hydrocarbons, in which most of the liquid hydrocarbons are held inside the micelles. See The Merck Index, Tenth Edition, Entry 7047, p. 1033 (1983); Schindler, *Drug. Cosmet. Ind.*, 89, 36–37, 76, 78–80, 82 (1961); and International Cosmetic Ingredient Dictionary, Fifth Edition, vol. 1, p. 537 (1993), which are incorporated by reference herein in their entirety.

Straight and branched chain hydrocarbons having from about 7 to about 40 carbon atoms are useful herein. Non-limiting examples of these hydrocarbon materials include dodecane, isododecane, squalane, cholesterol, hydrogenated polyisobutylene, docosane (i.e., a $C_{22}$ hydrocarbon), hexadecane, isohexadecane (a commercially available hydrocarbon sold as Permethyl® 101A by Presperse, South Plainfield, N.J.). Also useful are the C7–C40 isoparaffins, which are C7–C40 branched hydrocarbons.

Useful oils include C1–C30 alcohol esters of C1–C30 carboxylic acids and of C2–C30 dicarboxylic acids, including straight and branched chain materials as well as aromatic derivatives. Also useful are esters such as monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, and propylene glycol diesters of C1–C30 carboxylic acids. Straight chain, branched chain and aryl carboxylic acids are included herein. Also useful are propoxylated and ethoxylated derivatives of these materials. Nonlimiting examples include diisopropyl sebacate, diisopropyl adipate, isopropyl myristate, isopropyl palmitate, myristyl propionate, ethylene glycol distearate, 2-ethylhexyl palmitate, isodecyl neopentanoate, $C_{12-15}$ alcohols benzoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, caprilic/capric triglyceride, PEG-6 caprylic/capric triglyceride, PEG-8 caprylic/capric triglyceride, and mixtures thereof.

Also useful are various C1–C30 monoesters and polyesters of sugars and related materials. These esters are derived from a sugar or polyol moiety and one or more carboxylic acid moieties. Depending on the constituent acid and sugar, these esters can be in either liquid or solid form at room temperature. Examples of liquid esters include: glucose tetraoleate, the glucose tetraesters of soybean oil fatty acids (unsaturated), the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof. Examples of solid esters include: sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio. A preferred solid material is sucrose polyester in which the degree of electrification is 7–8, and in which the fatty acid moieties are C18 mono- and/or di-unsaturated and behenic, in a molar ratio of unsaturates:behenic of 1:7 to 3:5. A particularly preferred solid sugar polyester is the octaester of sucrose in which there are about 7 behenic fatty acid moieties and about 1 oleic acid moiety in the molecule. The ester materials are further described in, U.S. Pat. No. 2,831,854, U.S. Pat. No. 4,005,196, to Jandacek, issued Jan. 25, 1977; U.S. Pat. No. 4,005,195, to Jandacek, issued Jan. 25, 1977, U.S. Pat. No. 5,306,516, to Letton et al., issued Apr. 26, 1994; U.S. Pat. No. 5,306,515, to Letton et al., issued Apr. 26, 1994; U.S. Pat. No. 5,305,514, to Letton et al., issued Apr. 26, 1994; U.S. Pat. No. 4,797,300, to Jandacek et al., issued Jan. 10, 1989; U.S. Pat. No. 3,963,699, to Rizzi et al, issued Jun. 15, 1967; U.S. Pat. No. 4,518,772, to Volpenhein, issued May 21, 1985; and U.S. Pat. No. 4,517,360, to Volpenhein, issued May 21, 1985; all of which are incorporated by reference herein in their entirety.

Silicones such as polydialkylsolixanes, polydiarylsiloxanes, polyalkarylsiloxanes, and cyclomethicones having 3 to 9 silicon atoms are useful oils. These silicones include both volatile and nonvolatile materials. These silicones are disclosed in U.S. Pat. No. 5,069,897, to Orr, issued Dec. 3, 1991, which is incorporated by reference herein in its entirety. The polyalkylsiloxanes include, for example, polyalkylsiloxanes with viscosities of from 0.5 to about 100,000 centistokes at 25° C. Such polyalkylsiloxanes correspond to the general chemical formula $R_3SiO[R_2SiO]_xSiR_3$ wherein R is an alkyl group (preferably R is methyl or ethyl, more preferably methyl) and x is an integer from 0 to about 500, chosen to achieve the desired molecular weight. Commercially available polyalkylsiloxanes include the polydimethylsiloxanes, which are also known as dimethicones, nonlimiting examples of which include the Vicasil® series sold by General Electric Company and the Dow Corning® 200 series sold by Dow Corning Corporation. Specific examples of polydimethylsiloxanes useful as emollients herein include Dow Corning® 200 fluid having a viscosity of 0.65 centistokes and a boiling point of 100° C., Dow Corning® 225 fluid having a viscosity of 10 centistokes and a boiling point greater than 200° C., and Dow Corning® 200 fluids having viscosities of 50, 350, and 12,500 centistokes, respectively, and boiling points greater than 200° C. Cyclic polyalkylsiloxanes useful herein include those corresponding to the general chemical formula $[SiR_2-O]_n$ wherein R is an alkyl group (preferably R is methyl or ethyl, more preferably methyl) and n is an integer from about 3 to about 9, more preferably n is an integer from about 3 to about 7, and most preferably n is an integer from about 4 to about 6. When R is methyl, these materials are typically referred to as cyclomethicones. Commercially available cyclomethicones include Dow Corning® 244 fluid having a viscosity of 2.5 centistokes, and a boiling point of 172° C., which primarily contains the cyclomethicone tetramer (i.e. n=4), Dow Corning® 344 fluid having a viscosity of 2.5 centistokes and a boiling point of 178° C., which primarily contains the cyclomethicone pentamer (i.e. n=5), Dow Corning® 245 fluid having a viscosity of 4.2 centistokes and a boiling point of 205° C., which primarily contains a mixture of the cyclomethicone tetramer and pentamer (i.e. n=4 and 5), and Dow Corning® 345 fluid having a viscosity of 4.5 centistokes and a boiling point of 217°, which primarily contains a mixture of the cyclomethicone tetramer, pentamer, and hexamer (i.e. n=4, 5, and 6). Also useful are materials such as trimethylsiloxysilicate, which is a polymeric material corresponding to the general chemical formula $[(CH_2)_3SiO_{1/2}]_x[SiO_2]_y$, wherein x is an integer from about 1 to about 500 and y is an integer from about 1 to about 500. A commercially available trimethylsiloxysilicate is sold as a mixture with dimethicone as Dow Corning® 593 fluid. Also useful herein are dimethiconols, which are hydroxy terminated dimethyl silicones. These materials can be represented by the general chemical formulas $R_3SiO[R_2SiO]_xSiR_2OH$ and $HOR_2SiO[R_2SiO]_xSiR_2OH$ wherein R is an alkyl group (preferably R is methyl or ethyl, more preferably methyl) and x is an integer from 0 to about 500, chosen to achieve the desired molecular weight. Commercially available dimethiconols are typically sold as mixtures with dimethicone or cyclomethicone (e.g. Dow Corning® 1401, 1402, and 1403 fluids). Also useful herein are polyalkylaryl siloxanes, with polymethylphenyl siloxanes having viscosities from about 15 to about 65 centistokes at 25° C. being preferred. These materials are available, for example, as SF 1075 methylphenyl fluid (sold by General Electric Company) and 556 Cosmetic Grade phenyl trimethicone fluid (sold by Dow Corning Corporation).

Vegetable oils and hydrogenated vegetable oils are also used herein. Examples of vegetable oils and hydrogenated vegetable oils include safflower oil, castor oil, coconut oil, cottonseed oil, menhaden oil, palm kernel oil, palm oil, peanut oil, soybean oil, rapeseed oil, linseeed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

Also useful are polypropylene glycols, C4–C20 alkyl ethers of polypropylene glycols, C1–C20 carboxylic acid esters of polypropylene glycols, and di-C8–C30 alkyl ethers. Nonlimiting examples of these materials include PPG-14 butyl ether, PPG-15 stearyl ether, PPG-9, PPG-12, PPG-15, PPG-17, PPG-20, PPG-26, PPG-30, PPG-34, dioctyl ether, dodecyl octyl ether, and mixtures thereof.

Sunscreens and Tanning Agents

Also useful herein are sunscreening agents. A wide variety of sunscreening agents are described in U.S. Pat. No. 5,087,445, to Haffey et al., issued Feb. 11, 1992; U.S. Pat. No. 5,073,372, to Turner et al., issued Dec. 17, 1991; U.S. Pat. No. 5,073,371, to Turner et al. issued Dec. 17, 1991; and Segarin, et al., at Chapter VIII, pages 189 et seq., of *Cosmetics Science and Technology*, all of which are incorporated herein by reference in their entirety. Nonlimiting examples of sunscreens which are useful in the compositions of the present invention are those selected from the group consisting of 2-ethylhexyl p-methoxycinnamate, 2-ethylhexyl N,N-dimethyl-p-aminobenzoate, p-aminobenzoic acid, 2-phenylbenzimidazole-5-sulfonic acid, octocrylene, oxybenzone, homomenthyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Still other useful sunscreens are those disclosed in U.S. Pat. No. 4,937,370, to Sabatelli, issued Jun. 26, 1990; and U.S. Pat.

No. 4,999,186, to Sabatelli et al., issued Mar. 12, 1991; these two references are incorporated by reference herein in their entirety. The sunscreening agents disclosed therein have, in a single molecule, two distinct chromophore moieties which exhibit different ultraviolet radiation absorption spectra. One of the chormophore moieties absorbs predominantly in the UVB radiation range and the other absorbs strongly in the UVA radiation range. These sunscreening agents provide higher efficacy, broader UV absorption, lower skin penetration and longer lasting efficacy relative to conventional sunscreens. Especially preferred examples of these sunscreens include those selected from the group consisting of 4-N,N-(2-ethylhexyl)methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl)-methylaminobenzoic acid ester of 2-hydroxy-4-(2-hydroxyethoxy)benzophenone, 4-N,N-(2-ethylhexyl)-methylaminobenzoic acid ester of 4-(2-hydroxyethyoxy) dibenzoylmethane, and mixtures thereof. Generally, the sunscreens can comprise from about 0.5% to about 20% of the compositions useful herein. Exact amounts will vary depending upon the sunscreen chosen and the desired Sun Protection Factor (SPF). SPF is a commonly used measure of photoprotection of a sunscreen against erythema. See *Federal Register*, Vol. 43, No. 166, pp. 38206–38269, Aug. 25, 1978, which is incorporated herein by reference in its entirety.

Examples of artificial tanning agents and accelerators include dihydroxyacetone, tyrosine, tyrosine esters such as ethyl tyrosinate, and phospho-DOPA.

Method of Forming the Complex

The complex that is believed to be formed between the amphoteric and anionic surfactants of the present invention is preferably preformed and added to the active ingredient and any remaining components of the compositions of the present invention. The amphoteric and anionic surfactants are preferably combined in aqueous solution, thereby forming what is believed to be an aqueous dispersion of the complex.

Methods of Treating the Skin

The present invention also relates to methods wherein an effective amount of the composition of the present invention is applied to the skin. These compositions are useful for delivering active ingredients to the skin. A wide range of quantities of the compositions of the present invention can be used. Quantities which are typically applied can range from about 0.1 mg/cm$^2$ to about 25 mg/cm$^2$.

In preferred embodiments, the compositions of the present invention are also useful for person cleansing, especially for cleansing of the face and neck areas. Typically, a suitable or effective amount of the cleansing composition is applied to the area to be cleansed. Alternatively, a suitable amount of the cleansing composition can be applied via intermediate application to a washcloth, sponge, pad, cotton ball or other application device. If desired, the area to be cleansed can be premoistened with water. It has been found that the compositions of the present invention can be combined with water during the cleansing process and rinsed-off from the skin. Alternatively, the composition can be used alone and wiped-off from the skin using a pad, cotton ball, tissue, or other like device. The cleansing process is typically a two-step process involving application of the composition followed either by rinsing of the product with water or wiping without the use of water. Generally, an effective amount of composition to be used will depend upon the needs and usage habits of the individual.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Example 1

A leave-on lotion composition containing salicylic acid is prepared by combining the following ingredients using conventional mixing techniques.

| Ingredients | Weight Percent |
| --- | --- |
| Phase A | |
| Water | QS 100 |
| Glycerin | 3.00 |
| Tetrasodium EDTA | 0.02 |
| Phase B | |
| PPG-15 Stearyl Ether | 4.00 |
| Stearyl Alcohol | 0.75 |
| Salicylic Acid | 2.00 |
| Cetyl Alcohol | 0.75 |
| Steareth-21 | 0.45 |
| Steareth-2 | 0.05 |
| Dimethicone | 0.60 |
| Polyquaternium-37 (and) Mineral Oil (and) PPG-1 Trideceth-6 | 1.50 |
| Phase C | |
| Triethanolamine | 0.15 |
| Phase D | |
| Fragrance | 0.10 |
| Phase E | |
| Cetyl Dimethyl Betaine | 2.00 |
| Sodium Lauryl Sulfate | 1.00 |

In suitable vessel, the Phase A ingredients are heated with stirring to about 75° C. In a separate vessel, the Phase B ingredients are heated with stirring to about 75° C. Phase B is then added to Phase A with mixing. Next Phase C is added with mixing. Next the fragrance is added with mixing. Next, the mixture is cooled to 35° C. In a separate vessel, the Phase E ingredients are combined and added to the remaining mixture with stirring.

The resulting leave-on composition is useful for preventing and treating acne while being mild to the skin.

Alternatively, a composition is prepared in which the sodium lauryl sulfate is replace with sodium lauroyl isethe-onate.

Example 2

A personal cleanser composition containing salicylic acid is prepared by combining the following ingredients using conventional mixing techniques.

| Ingredients | Weight Percent |
| --- | --- |
| Phase A | |
| Water | QS 100 |
| Glycerin | 3.00 |
| Disodium EDTA | 0.01 |
| Phase B | |
| PPG-15 Stearyl Ether | 4.00 |
| Stearyl Alcohol | 2.88 |
| Salicylic Acid | 2.00 |
| Cetyl Alcohol | 0.80 |
| Distearyl Dimethyl Ammonium Chloride | 1.50 |
| Steareth-21 | 0.50 |
| Behenyl Alcohol | 0.32 |
| PPG-30 | 0.25 |
| Steareth-2 | 0.25 |
| Phase C | |
| Oxidized Polyethylene Beads[1] | 1.00 |
| Fragrance | 0.27 |
| Phase D | |
| Cocamidopropyl Betaine | 2.00 |
| Sodium Lauryl Sulfate | 1.00 |

[1]Available as Acucscrub ™ 51 from Allied Signal Corporation.

In a suitable vessel, the Phase A ingredients are heated with stirring to about 75° C. In a separate vessel, the Phase B ingredients are heated with stirring to about 75° C. Phase B is then added to Phase A with mixing. Next, the oxidized polyethylene beads are added slowly with mixing to prevent agglomeration. Next the fragrance is added with mixing. Next, the mixture is cooled to 35° C. In a separate vessel, the Phase D ingredients are combined and added to the remaining mixture with stirring.

The resulting cleansing composition is useful for cleansing the skin.

Alternatively, a composition is prepared in which the sodium lauryl sulfate is replaced with sodium lauroyl isetheonate.

Alternatively, a composition is prepared in which the salicylic acid is replaced with 2.5% benozyl peroxide, with the water being adjust accordingly.

Example 3

A person cleanser composition containing salicylic acid and menthol is prepared by combining the following ingredients using conventional mixing techniques.

| Ingredients | Weight Percent |
| --- | --- |
| Phase A | |
| Water | QS 100 |
| Glycerin | 3.00 |
| Disodium EDTA | 0.01 |
| Phase B | |
| PPG-15 Stearyl Ether | 4.00 |
| Stearyl Alcohol | 2.88 |
| Salicylic Acid | 2.00 |
| Distearyl Dimethyl Ammonium Chloride | 1.50 |
| Cetyl Alcohol | 0.80 |
| Steareth-21 | 0.50 |
| Behenyl Alcohol | 0.32 |
| PPG-30 | 0.25 |
| Steareth-2 | 0.25 |
| Phase C | |
| Oxidized Polyethylene Beads[1] | 1.00 |
| Fragrance | 0.27 |
| Menthol | 0.05 |
| Phase D | |
| Cetyl Dimethyl Betaine | 2.00 |
| Sodium Lauryl Sulfate | 1.00 |

[1]Available as Acucscrub ™ 51 from Allied Signal Corporation.

In a suitable vessel, the Phase A ingredients are heated with stirring to about 75° C. In a separate vessel, the Phase B ingredients are heated with stirring to about 75° C. Phase B is then added to Phase A with mixing. Next, the oxidized polyethylene beads are added slowly with mixing to prevent agglomeration. Next the fragrance and menthol are added with mixing. Next, the mixture is cooled to 35° C. In a separate vessel, the Phase D ingredients are combined and added to the remaining mixture with stirring.

The resulting cleansing composition is useful for cleansing the skin.

Alternatively, a composition is prepared in which the sodium lauryl sulfate is replace with sodium lauroyl isetheonate.

Alternatively, a composition is prepared in which the salicylic acid is replaced with 2.5% benzoyl peroxide with the water being adjusted correspondingly.

Example 4

A leave-on lotion composition containing benzoyl peroxide is prepared by combining the following ingredients using convention mixing techniques.

| Ingredients | Weight Percent |
| --- | --- |
| Phase A | |
| Water | QS 100 |
| Glycerin | 4.00 |
| Disodium EDTA | 0.10 |
| Carbomer | 0.60 |
| Acrylates/C10–30 Alkylacrylates Crosspolymer | 0.05 |
| Phase B | |
| Stearyl Alcohol | 2.25 |
| Cetyl Alcohol | 2.25 |
| Steareth-100 | 0.50 |
| Glyceryl Hydroxystearate | 0.74 |
| Dimethicone | 0.60 |
| Phase C | |
| Triethanolamine | 0.50 |
| Phase D | |
| Benzoyl Peroxide | 2.50 |
| Phase E | |
| Cetyl Dimethyl Betaine | 1.00 |
| Sodium Lauryl Sulfate | 0.50 |

In a suitable vessel, the Phase A ingredients are heated with stirring to about 75° C. In a separate vessel, the Phase B ingredients are heated with stirring to about 75° C. Phase B is then added to Phase A with mixing. Next Phase C is added with mixing. Next, the mixture is cooled to 35° C. Next the benzoyl peroxide is added with mixing. In a separate vessel, the Phase E ingredients are combined and added to the remaining mixture with stirring.

The resulting leave-on composition is useful for preventing and treating acne while being mild to the skin.

Alternatively, a composition is prepared in which the cetyl dimethyl betaine is replaced with stearyl dimethyl betaine.

Example 5

A personal cleansing gel composition containing glycolic acid is prepared by combining the following ingredients using convention mixing techniques.

| Ingredients | Weight Percent |
|---|---|
| Phase A | |
| Water | QS 100 |
| Glycerin | 4.00 |
| Disodium EDTA | 0.10 |
| Dimethicone | 0.20 |
| PVM/MA Decadiene Crosspolymer | 1.00 |
| Glycolic Acid | 2.00 |
| Sodium Hydroxide | 0.80 |
| Phase B | |
| Cetyl Dimethyl Betaine | 1.00 |
| Sodium Lauryl Sulfate | 0.50 |

In a suitable vessel, the Phase A ingredients are mixed vigorously. In a separate vessel, the Phase B ingredients are combined and added to the remaining mixture with stirring.

The resulting cleansing gel composition is useful for reducing the appearance of pore size while being mild to the skin and cleansing effectively.

Alternatively, a composition is prepared in which glycolic acid is replaced with salicylic acid and the resulting composition is useful for preventing and treating acne and blemished while being mild to the skin and cleansing effectively.

Alternatively, a composition is prepared in which the cetyl dimethyl betaine is replaced with cocamidopropyl betaine.

What is claimed is:

1. A topical personal care composition comprising:
   (a) from about 0.1% to about 20% by weight of an amphoteric surfactant having the following structure

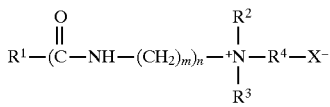

wherein $R^1$ is unsubstituted, saturated or unsaturated, straight or branched chain alkyl having from about 9 to about 22 carbon atoms; m is an integer from 1 to about 3; n is 0 or 1; $R^2$ and $R^3$ are independently selected from alkyl having from 2 to about 3 carbon atoms and monohydroxy-alkyl having from 1 to about 3 carbon atoms; $R^2$ is selected from saturated or unsaturated alkyl having from 1 to about 5 carbon atoms and saturated or unsaturated monohydroxy-alkyl having from 1 to about 5 carbon atoms; X is selected from the group consisting of $CO_2$, $SO_3$, and $SO_4$; and pharmaceutically acceptable salts of the foregoing compounds;
   (b) from about 0.1% to about 20% by weight of an anionic surfactant,
   (c) from about 0.001% to about 20% of an active ingredient,
   (d) from about 0.25% to about 40% of an oil, and
   (e) from about 40% to about 95% by weight water.

2. A composition according to claim 1 wherein said oil comprises from about 0.5% to about 25% by weight of said composition.

3. A composition according to claim 2 wherein said oil comprises from about 0.75% to about 15% by weight of said composition.

4. A composition according to claim 1 wherein said oil is selected from the group consisting of mineral oil, petrolatum, C7–C40 straight and branched chain hydrocarbons, C1–C30 alcohol esters of C1–C30 carboxylic acids, C1–C30 alcohol esters of C2–C30 dicarboxylic acids, monoglycerides of C1–C30 carboxylic acids, diglycerides of C1–C30 carboxylic acids, triglycerides of C1–C30 carboxylic acids, ethylene glycol monoesters of C1–C30 carboxylic acids, ethylene glycol diesters of C1–C30 carboxylic acids, propylene glycol monoesters of C1–C30 carboxylic acids, propylene glycol diesters of C1–C30 carboxylic acids, C1–C30 carboxylic acid monoesters and polyesters of sugars, silicones, vegetable oils, hydrogenated vegetable oils, polypropylene glycols, polypropylene glycol C4–C20 alkyl ethers, di C8–C30 alkyl ethers, and mixtures thereof.

5. A composition according to claim 4 wherein said C7–C40 straight and branched chain hydrocarbon is selected from the group consisting of dodecane, isododecane, squalane, cholesterol, hydrogenated polyisobutylene, docosane, hexadecane, isohexadecane, C7–$C_{40}$ isoparaffins, and mixtures thereof.

6. A composition according to claim 4 wherein said oil is selected from the group consisting of diisopropyl sebacate, diisopropyl adipate, isopropyl myristate, isopropyl palmitate, myristyl propionate, ethylene glycol distearate, 2-ethylhexyl palmitate, isodecyl copentanoate, $C_{12-15}$ alcohols benzoate, di-2-ethylhexyl maleate, cetyl palmitate, myristyl myristate, stearyl stearate, cetyl stearate, behenyl behenrate, dioctyl maleate, dioctyl sebacate, diisopropyl adipate, cetyl octanoate, diisopropyl dilinoleate, caprilic/capric triglyceride, PEG-6 caprylic/capric triglyceride, PEG-8 caprylic/capric triglyceride, and mixtures thereof.

7. A composition according to claim 4 wherein said C1–C30 carboxylic acid monoesters and polyesters of sugars are selected from the group consisting of liquid esters, solid esters, and mixtures thereof.

8. A composition according to claim 7 wherein said liquid esters are selected from the group consisting of glucose tetraoleate, the glucose tetraesters of soybean oil fatty acids, the mannose tetraesters of mixed soybean oil fatty acids, the galactose tetraesters of oleic acid, the arabinose tetraesters of linoleic acid, xylose tetralinoleate, galactose pentaoleate, sorbitol tetraoleate, the sorbitol hexaesters of unsaturated soybean oil fatty acids, xylitol pentaoleate, sucrose tetraoleate, sucrose pentaoletate, sucrose hexaoleate, sucrose hepatoleate, sucrose octaoleate, and mixtures thereof.

9. A composition according to claim 7 wherein said solid esters are selected from the group consisting of sorbitol hexaester in which the carboxylic acid ester moieties are palmitoleate and arachidate in a 1:2 molar ratio; the octaester of raffinose in which the carboxylic acid ester moieties are linoleate and behenate in a 1:3 molar ratio; the heptaester of maltose wherein the esterifying carboxylic acid moieties are sunflower seed oil fatty acids and lignocerate in a 3:4 molar ratio; the octaester of sucrose wherein the esterifying carboxylic acid moieties are oleate and behenate in a 2:6 molar ratio; and the octaester of sucrose wherein the esterifying carboxylic acid moieties are laurate, linoleate and behenate in a 1:3:4 molar ratio; and mixtures thereof.

10. A composition according to claim 7 wherein said solid ester is a sucrose polyester in which the degree of esterification is 7–8, and in which the fatty acid moieties are C18 mono- and/or di-unsaturated and behenic, in a molar ratio of unsaturates:behenic of 1:7 to 3:5.

11. A composition according to claim 7 wherein said solid ester is an octaester of sucrose in which there are about 7 behenic fatty acid moieties and about 1 oleic acid moiety in the molecule; and mixtures thereof.

12. A composition according to claim 4 wherein said silicones are selected from the group consisting of polyalkylsiloxanes, polydialkylsiloxanes, cyclic polyalkylsiloxanes, polydiarylsiloxanes, polyalkarylsiloxanes, cyclomethicones having 3 to 9 silicone atoms, trimethylsiloxysilicates, dimethiconols, and mixtures thereof.

13. A composition according to claim 12 wherein said polyalkylsiloxane corresponds to the general chemical formula $R_3SiO[R_2SiO]_xSiR_3$,
wherein R is an alkyl group, and x is an integer from 0 to about 500.

14. A composition according to claim 13 wherein R is methyl or ethyl.

15. A composition according to claim 12 wherein said cyclic polyalkylsiloxane corresponds to the general chemical formula $[SiR_2-O]_n$,
wherein R is an alkyl group, and n is an integer from about 3 to about 9.

16. A composition according to claim 15 wherein R is methyl or ethyl.

17. A composition according to claim 12 wherein said trimethylsiloxysilicate corresponds to the general chemical formula $[(CH_3)_3SiO_{1/2}]_x[SiO_2]_y$,
wherein x is an integer from about 1 to about 500 and y is an integer from about 1 to about 500.

18. A composition according to claim 12 wherein said dimethiconol corresponds to the general chemical formulas $R_3SiO[R_2SiO]_xSiR_2OH$ and $HOR_2SiO[R_2SiO]_xSiR_2OH$,
wherein R is an alkyl group, and x is an integer from 0 to about 500.

19. A composition according to claim 18 wherein R is methyl or ethyl.

20. A composition according to claim 4 wherein said vegetable oils and hydrogenated vegetable oils are selected from the group consisting of safflower oil, castor oil, coconut oil, cottonseed oil, menhaden oil, palm kernel oil, palm oil, peanut oil, soybean oil, rapeseed oil, linseed oil, rice bran oil, pine oil, sesame oil, sunflower seed oil, hydrogenated safflower oil, hydrogenated castor oil, hydrogenated coconut oil, hydrogenated cottonseed oil, hydrogenated menhaden oil, hydrogenated palm kernel oil, hydrogenated palm oil, hydrogenated peanut oil, hydrogenated soybean oil, hydrogenated rapeseed oil, hydrogenated linseed oil, hydrogenated rice bran oil, hydrogenated sesame oil, hydrogenated sunflower seed oil, and mixtures thereof.

21. A composition according to claim 4 wherein said polypropylene glycols, said polypropylene glycol C4–C20 alkyl esters, and said di C8–C30 alkyl esters are selected from the group consisting of PPG-14 butyl ether, PPG-15 stearyl ether, PPG-9, PPG-12, PPG-15, PPG-17, PPG-20, PPG-26, PPG-30, PPG-34, dioctyl ether, dodecyl octyl ether, and mixtures thereof.

22. A composition according to claim 1 wherein said active ingredient is selected from the group consisting of anti-acne actives, anti-wrinkle actives, anti-skin atrophy actives, non-steroidal anti-inflammatory actives, topical anesthetics, antimicrobial actives, antifungal actives, and mixtures thereof.

* * * * *

UNITED STATES PATENT AND TRADEMARK OFFICE
CERTIFICATE OF CORRECTION

PATENT NO. : 5,811,111

DATED : September 22, 1998

INVENTOR(S) : David Michael McAtee et al.

It is certified that error appears in the above-identified patent and that said Letters Patent is hereby corrected as shown below:

At column 1, line 21 "many year" should read --many years--.

At column 1, line 22 "supple conditions" should read --supple condition--.

At column 2, line 2 "folicular" should read --follicular--.

At column 2, line 4 "bateria" should read --bacteria--.

At column 2, line 10 "off the excess" should read --off of excess--.

At column 2, line 25 "these composition" should read --these compositions--.

At column 4, line 36 "in the form" should read --in a form--.

At column 5, line 22 "steryl" should read --stearyl--.

At column 5, line 28 "2_hydroxyethyl" should read --2-hydroxyethyl--.

At column 5, line 36 "Miratain" should read --Mirataine--.

At column 5, line 47 "Preferred $R^2$" should read --Preferred $R^1$--.

At column 5, line 61 "carbons atoms" should read --carbon atoms--, at both occurrences.

At column 6, line 22 "carbons atoms" should read --carbon atoms--.

At column 6, line 40 "dimethyl betaines" should read --dimethyl betaine--.

At column 7, line 28 "triethanoloamine" should read --triethanolamine--.

At column 7, line 53 "palm oil coconut" should read --palm oil, coconut--.

At column 8, line 20 "medial judgment" should read --medical judgement--.

At column 8, lines 20-21 "amount of active" should read --amount of the active--.

At column 8, line 53 "actopirox" should read --octopirox--.

At column 8, line 54 "2°-hydroxy" should read --2'-hydroxy--.

At column 9, line 13 "microprofen" should read --miroprofen--.

UNITED STATES PATENT AND TRADEMARK OFFICE
CERTIFICATE OF CORRECTION

PATENT NO.    :    5,811,111
DATED         :    September 22, 1998
INVENTOR(S)   :    David Michael McAtee et al.

It is certified that error appears in the above-identified patent and that said Letters Patent is hereby corrected as shown below:

At column 9, line 14 "bucloxis acid" should read --bucloxic acid--.

At column 9, line 30 "chorhexidine" should read --chlorhexidine--.

At column 9, line 33 "methanamine" should read --methenamine--.

At column 9, line 36 "hydrochoride" should read --hydrochloride--.

At column 10, line 1 "N-acetyl-L-cystein" should read --N-acetyl-L-cysteine--.

At column 10, line 13 "2,4,4,'-trichloro" should read --2,4,4'-trichloro--.

At column 10, line 14 "3,4,4,'-trichlorocarbanilide" should read --3,4,4'-trichlorocarbanilide--.

At column 10, line 20 "composition" should read --compositions--.

At column 10, line 44 "platicizers" should read --plasticizers--.

At column 10, line 63 "dimethocone" should read --dimethicone--.

At column 11, line 10 "pantaerythritol" should read --pentaerythritol--.

At column 11, line 12 "CTGA" should read --CTFA--.

At column 11, line 18 "coloring" should read --colorings--.

At column 11, line 39 "more preferably" should read --most preferably--.

At column 12, line 5 "either linkages" should read --ether linkages--.

At column 12, line 7 "polyproylene" should read --polypropylene--.

At column 12, line 8 "$R_2$" should read --$R_1$--.

At column 12, line 10 "carbons atoms" should read --carbon atoms--.

At column 12, line 14 "$R_2$" should read --$R_1$--.

At column 12, line 16 "X is a described" should read --X is as described--.

At column 12, line 18 "$R_2$" should read --$R_1$--.

UNITED STATES PATENT AND TRADEMARK OFFICE
CERTIFICATE OF CORRECTION

PATENT NO. : 5,811,111

DATED : September 22, 1998

INVENTOR(S) : David Michael McAtee et al.

It is certified that error appears in the above-identified patent and that said Letters Patent is hereby corrected as shown below:

At column 12, line 44 "diectyl" should read --dicetyl--.

At column 12, line 45 "decetyl" should read --dicetyl--.

At column 12, line 53 "wherein C12" should read --wherein the C12--.

At column 12, line 61 "slats" should read --salts--.

At column 13, line 18 "more preferably" should read --most preferably--.

At column 13, line 27 "what are useful" should read --that are useful--.

At column 13, line 28 "those than can" should read --those that can--.

At column 15, line 2 "or Orr et al." should read --to Orr et al.--.

At column 15, line 35 "means particle" should read --mean particle--.

At column 15, line 48 "means particle" should read --mean particle--.

At column 16, line 8 "soy four" should read --soy flour--.

At column 16, line 22 "methylebisacrylamide" should read --methylenebisacrylamide--.

At column 16, line 45 "include Propyltex" should read --include the Propyltex--.

At column 17, line 14 "there four" should read --these four--.

At column 17, line 34 "10% more" should read --10%, more--.

At column 19, lines 5-6 "electrification" should read --esterification--.

At column 19, lines 19-20 "Jun. 15, 1967" should read --Jun. 15, 1976--.

At column 19, line 24 "polydialkylsolixanes" should read --polydialkylsiloxanes--.

At column 19, line 31 "from 0.5" should read --from about 0.5--.

At column 20, line 27 "used herein" should read --useful herein--.

At column 20, line 30 "linseeed oil" should read --linseed oil--.

UNITED STATES PATENT AND TRADEMARK OFFICE
CERTIFICATE OF CORRECTION

PATENT NO. : 5,811,111

DATED : September 22, 1998

INVENTOR(S) : David Michael McAtee et al.

It is certified that error appears in the above-identified patent and that said Letters Patent is hereby corrected as shown below:

At column 21, line 6 "chormophore" should read --chromophore--.

At column 21, line 19 "2-hydroxyethyoxy" should read --2-hydroxyethoxy--.

At column 21, line 53 "person cleansing" should read --personal cleansing--.

At column 22, line 48 "In suitable" should read --In a suitable--.

At column 22, line 60 "is replace with" should read --is replaced with--.

At column 23, line 42 "being adjust" should read --being adjusted--.

At column 23, line 46 "person cleanser" should read --personal cleanser--.

At column 24, line 24 "is replace with" should read --is replaced with--.

At column 24, line 33 "convention mixing" should read --conventional mixing--.

At column 25, line 7 "convention mixing" should read --conventional mixing--.

At column 25, line 32 "blemished" should read --blemishes--.

At column 25, line 50 "from 2 to" should read --from 1 to--.

At column 25, line 51 "$R^2$ is selected" should read --$R^4$ is selected--.

At column 26, line 22 "C7–$C_{40}$" should read --C7–C40--.

At column 26, line 28 "copentanoate" should read --neopentanoate--.

At column 27, line 30 "1to" should read --1 to--.

UNITED STATES PATENT AND TRADEMARK OFFICE
CERTIFICATE OF CORRECTION

PATENT NO. : 5,811,111
DATED : September 22, 1998
INVENTOR(S) : David Michael McAtee et al.

It is certified that error appears in the above-identified patent and that said Letters Patent is hereby corrected as shown below:

At column 28, line 21 "esters" should read --ethers--, at both occurrences.

Signed and Sealed this

Twenty-third Day of February, 1999

Attest:

Q. TODD DICKINSON

Attesting Officer

Acting Commissioner of Patents and Trademarks